US011957831B2

United States Patent
Säll et al.

(10) Patent No.: US 11,957,831 B2
(45) Date of Patent: Apr. 16, 2024

(54) ACTIVATION MECHANISM FOR AN AEROSOL DISPENSER

(71) Applicant: SHL MEDICAL AG, Zug (CH)

(72) Inventors: Daniel Säll, Segeltorp (SE); Stefan Gylleby, Akersberga (SE)

(73) Assignee: SHL MEDICAL AG, Zug (CH)

( * ) Notice: Subject to any disclaimer, the term of this patent is extended or adjusted under 35 U.S.C. 154(b) by 603 days.

(21) Appl. No.: 17/275,610

(22) PCT Filed: Sep. 13, 2019

(86) PCT No.: PCT/EP2019/074569
§ 371 (c)(1),
(2) Date: Mar. 11, 2021

(87) PCT Pub. No.: WO2020/064372
PCT Pub. Date: Apr. 2, 2020

(65) Prior Publication Data
US 2022/0054775 A1    Feb. 24, 2022

(30) Foreign Application Priority Data

Sep. 27, 2018  (EP) .................................. 18197285
Sep. 27, 2018  (EP) .................................. 18197289
(Continued)

(51) Int. Cl.
*A61M 15/00*    (2006.01)
*A61M 11/00*    (2006.01)

(52) U.S. Cl.
CPC ........ *A61M 15/007* (2014.02); *A61M 11/006* (2014.02); *A61M 15/0081* (2014.02); *A61M 15/0096* (2014.02)

(58) Field of Classification Search
CPC .... A61M 15/00–0001; A61M 15/0065; A61M 15/0068–0073; A61M 15/0081; A61M 11/00; A61M 11/006–007
See application file for complete search history.

(56) References Cited

U.S. PATENT DOCUMENTS 5,511,538 A    4/1996 Haber et al.
5,964,416 A    10/1999 Jaeger et al.
(Continued)

FOREIGN PATENT DOCUMENTS

CN    1220622 A    6/1999
CN    101426531 A    5/2009
(Continued)

OTHER PUBLICATIONS

International Search Report and Written Opinion for Int. App. No. PCT/EP2019/074569, dated Nov. 26, 2019.

*Primary Examiner* — Rachel T Sippel
(74) *Attorney, Agent, or Firm* — MCDONNELL BOEHNEN HULBERT & BERGHOFF LLP

(57) ABSTRACT

An activation mechanism for an aerosol dispenser is presented having a first housing structure, an actuation member movably arranged in the first housing structure, wherein the first housing structure is provided with an actuation member opening in level with the axial position of the actuation member, and an activation member slidably attached to the first housing structure, the activation member slides between a non-triggering position and a triggering position relative to the first housing structure, wherein the activation member has a radially flexible tab portion that is offset from the actuation member opening when the activation member is in the non-triggering position, restricting radial flexing of the tab portion, and wherein the tab portion aligns with the actuation member opening when the activation member is in (Continued)

the triggering position, thereby enabling the tab portion to flex radially inwards to cause movement of the actuation member.

19 Claims, 14 Drawing Sheets

(30) Foreign Application Priority Data

Sep. 27, 2018 (EP) .................................... 18197299
Sep. 27, 2018 (EP) .................................... 18197311
Sep. 27, 2018 (EP) .................................... 18197317
Mar. 14, 2019 (EP) .................................... 19162982

(56) References Cited

U.S. PATENT DOCUMENTS

| | | |
|---|---|---|
| 2010/0237098 A1 | 9/2010 | Kaufman |
| 2011/0083666 A1 | 4/2011 | Eberhard |
| 2012/0090603 A1 | 4/2012 | Dunne et al. |
| 2017/0072148 A1* | 3/2017 | Eicher ................. B05B 11/0054 |
| 2019/0038850 A1 | 2/2019 | Kadel et al. |

FOREIGN PATENT DOCUMENTS

| | | |
|---|---|---|
| DE | 19708406 A1 | 9/1998 |
| WO | 97/20590 A1 | 6/1997 |
| WO | 2004/022244 A1 | 3/2004 |
| WO | 2015/003762 A1 | 1/2015 |
| WO | 2016/055438 A1 | 4/2016 |

* cited by examiner

ACTIVATION MECHANISM FOR AN AEROSOL DISPENSER

CROSS REFERENCE TO RELATED APPLICATIONS

The present application is a U.S. National Phase Application pursuant to 35 U.S.C. § 371 of International Application No. PCT/EP2019/074569 filed Sep. 13, 2019, which claims priority to European Patent Application No. 18197285.2 filed Sep. 27, 2018, European Patent Application No. 18197289.4 filed Sep. 27, 2018, European Patent Application No. 18197299.3 filed Sep. 27, 2018, European Patent Application No. 18197311.6 filed Sep. 27, 2018, European Patent Application No. 18197317.3 filed Sep. 27, 2018, and European Patent Application No. 19162982.3 filed Mar. 14, 2019. The entire disclosure contents of these applications are herewith incorporated by reference into the present application.

TECHNICAL FIELD

The present disclosure generally relates to aerosol dispensers.

BACKGROUND

Aerosol dispensers may be configured to provide multiple doses of a liquid such as a medicament. Devices of this type may be provided with an actuating button configured to activate the device.

U.S. Pat. No. 5,964,416 discloses an inhaler having a generally annular blocking member which is configured to move between an abutment and a support in the upper housing part. An actuating button is connected to the blocking member and can either move it bodily or deform it so that it releases the abutment to dispense a liquid.

One disadvantage with the design disclosed in U.S. Pat. No. 5,964,416 is that a dose may be dispensed in the event that a user accidentally reaches the actuation button during loading of the device.

SUMMARY

A general object of the present disclosure is to provide an activation mechanism for an aerosol dispenser which solves or at least mitigates problems of the prior art.

There is hence according to a first aspect of the present disclosure provided an activation mechanism for an aerosol dispenser, wherein the activation mechanism comprises: a first housing structure, an actuation member movably arranged in the first housing structure, wherein the first housing structure is provided with an actuation member opening in level with the axial position of the actuation member, and an activation member configured to be slidably attached to the first housing structure, the activation member being configured to slide between a non-triggering position and a triggering position relative to the first housing structure, wherein the activation member has a radially flexible tab portion, the tab portion being arranged offset from the actuation member opening when the activation member is in the non-triggering position, restricting radial flexing of the tab portion, and wherein the tab portion is configured to align with the actuation member opening when the activation member is in the triggering position, thereby enabling the tab portion to flex radially inwards to cause movement of the actuation member.

Hence, when the activation member is in the non-triggering position, the actuation member cannot be moved, or at least not significantly moved, by the activation member. The actuation member may be configured to prevent dose dispensing prior to it being moved by the activation member. In particular, the actuation member may obtain a blocking position when the activation member is in the non-triggering position and a release position when the tab portion moves the actuation member.

According to one embodiment the first housing structure has a central axis and the actuation member is movable in a transverse plane relative to the central axis.

According to one embodiment the actuation member is generally annular and arranged offset from the central axis when the activation member is in the non-triggering position.

According to one embodiment the actuation member has a radially outwards extending protrusion configured to extend into the actuation member opening and wherein the actuation member narrows radially on both peripheral sides of the protrusion.

According to one embodiment the actuation member is configured to be rotationally locked relative to the first housing structure.

One embodiment comprises an inner sleeve configured to be rotatably attached to the first housing structure.

One embodiment comprises a pump sleeve configured to be rotationally locked relative to the inner sleeve, wherein the pump sleeve is configured to be rotatable relative to the first housing structure and configured to move axially relative to the first housing structure and the inner sleeve, wherein the pump sleeve is configured to cooperate with the first housing structure such that rotation of the first housing structure relative to the inner sleeve causes axial displacement of the pump sleeve relative to the first housing structure and relative to the inner sleeve, the pump sleeve thereby moving from a default position to a loaded position.

According to one embodiment the actuation member is configured to lock the pump sleeve in the loaded position, and wherein the actuation member is configured to release the pump sleeve from the loaded position when moved by the tab portion.

According to one embodiment the inner sleeve has a radial flange surface, wherein the activation member is configured to rest on the flange surface, whereby rotation of the inner sleeve relative to the first housing structure causes movement of the activation member along the flange surface.

According to one embodiment the flange surface has an axial recess configured to receive a portion of the activation member when the inner sleeve is rotated relative to the first housing structure, thereby allowing movement of the activation member from the non-triggering position to the triggering position.

One embodiment comprises a dose counter configured to be arranged coaxially with the first housing structure and the inner sleeve, wherein the dose counter is configured to rotate relative to the first housing structure and the inner sleeve, the dose counter having a remaining dose scale and the dose counter being provided with an axial tab configured to bear against the activation member when the remaining dose scale indicates that no further doses are available, to prevent the activation member to move from the non-triggering position to the triggering position.

According to one embodiment the activation member has a guide heel arranged proximally relative to the axial tab, wherein the guide heel is configured to bear against the axial tab of the dose counter when the remaining dose scale indicates that no further doses are available.

According to one embodiment the activation member is configured to be biased towards the triggering position.

According to one embodiment the first housing structure is provided with an axially extending track and the activation member has wings configured to run in the track to guide sliding movement of the activation member.

There is according to a second aspect of the present disclosure provided an aerosol dispenser comprising an activation mechanism according to the first aspect.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
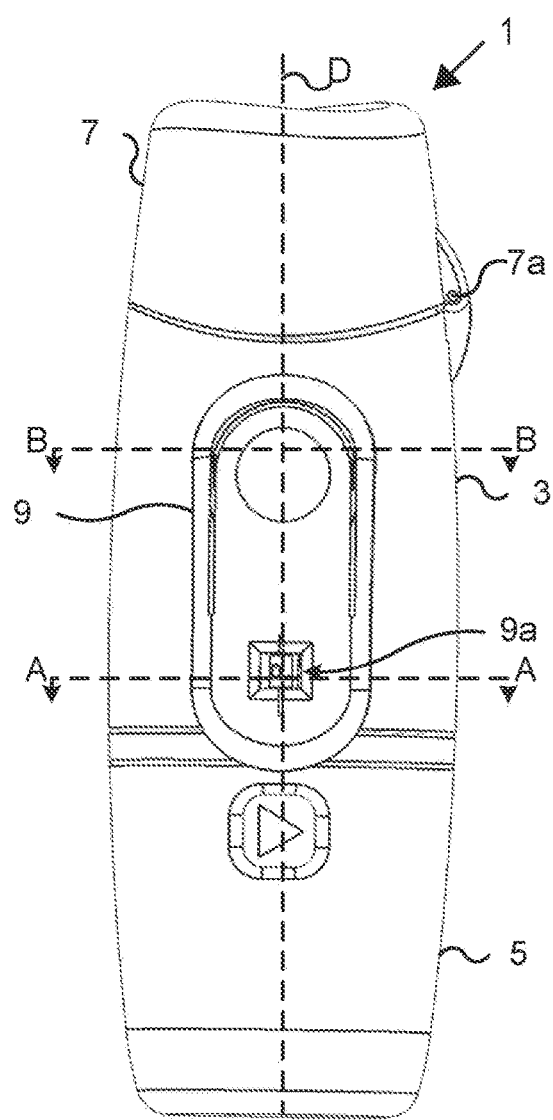
FIG. 1 shows a side view of an example of an aerosol dispenser.

FIG. 1 shows a perspective view of an example of an aerosol dispenser 1, such as an inhaler or an eye dispenser. The aerosol dispenser 1 comprises a first housing structure 3 and a second housing structure 5. The first housing structure 3 forms part of an external housing of the aerosol dispenser 1. The second housing structure 5 also forms part of the external housing of the aerosol dispenser 1. The second housing structure 5 may form a housing base.

In the example in FIG. 1, the first housing structure 3 and the second housing structure 5 have an elongated shape and are coaxially arranged. The central axis D of the first housing structure 3 and the second housing structure 5 coincide and form the central axis of the aerosol dispenser 1.

The exemplified aerosol dispenser 1 furthermore comprises an aerosol dispensing end cap 7 attached to the first housing structure 3. The aerosol dispensing end cap 7 forms an aerosol dispensing end of the aerosol dispenser 1. The aerosol dispensing end cap 7 is pivotally attached to the first housing structure 3. The aerosol dispensing end cap 7 is configured to be pivoted about a pivot axis 7a to open the aerosol dispenser 1 for a dispensing operation.

In the example shown in FIG. 1, the second housing structure 5 forms a distal end of the aerosol dispenser 1 and the aerosol dispensing end cap 7 forms a proximal end of the aerosol dispenser 1. The first housing structure 3 is arranged axially between the second housing structure 5 and the aerosol dispensing end cap 7. As used herein the "proximal direction" is a direction from the distal end towards the proximal end along an axis parallel with the central axis D. The "distal direction" is a direction opposite to the proximal direction.

The first housing structure 3 is configured to be rotatably attached to the second housing structure 5. The aerosol dispenser 1 is configured to be activated by rotation of the second housing structure 5 relative to the first housing structure 3. This rotation may for example be about 180 degrees. Thus, every time that the aerosol dispenser 1 is activated or loaded for a dispensing operation the second housing structure 5 is rotated a predetermined amount, such as 180 degrees, relative to the first housing structure 3.

The aerosol dispenser 1 furthermore comprises an activation member 9 configured to trigger an aerosol dispensing operation when the aerosol dispenser 1 has been activated or loaded. The activation member 9 may for example be a push/slide button. The activation member 9 is configured to be arranged in an opening in the first housing structure 3. The activation member 9 is configured to slide axially relative to the first housing structure 3 between a proximal non-triggering position and a distal triggering position. The activation member 9 can be further received by the first housing structure 3 in the triggering position. The activation member 9 is hence radially displaceable in the triggering position, and such radial displacement may be provided by pushing the activation member 9. By pushing the activation member 9 in the triggering position a dispensing operation is triggered. The activation member 9 is prevented from such radial displacement in the non-triggering position. Triggering of a dispensing operation is hence prevented.

The exemplified activation member 9 has a dose display 9a indicating the remaining number of doses. The dose display 9a may for example be a dose window.

Figure 2:
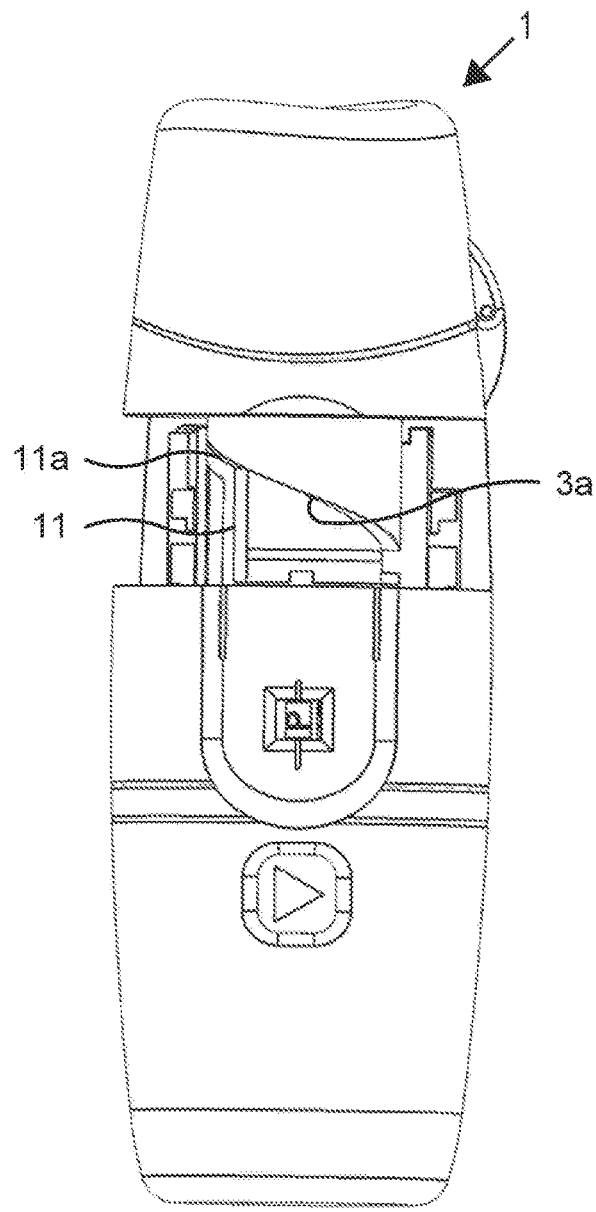
FIG. 2 is a side view of the aerosol dispenser in FIG. 1 with a cut-out portion to expose the interior of the aerosol dispenser.

FIG. 2 shows the aerosol dispenser 1 with part of the first housing structure 3 and the activation member 9 cut away to expose the interior of the aerosol dispenser 1. The aerosol dispenser 1 comprises an axially movable pump sleeve 11 configured to receive and engage with a cartridge. The pump sleeve 11 is configured to be rotationally locked relative to the second housing structure 5. The pump sleeve 11 is configured to be axially moveable relative to the first housing structure 3 and relative to the second housing structure 5.

The pump sleeve 11 is configured to cooperate with the first housing structure 3 such that rotation of the first housing structure 3 relative to the second housing structure 5 causes axial displacement of the pump sleeve relative to the first housing structure 3 and relative to the second housing structure 5. According to the example in FIG. 2, the translation of rotational motion of the first housing structure 3 to a linear motion of the pump sleeve 11 is obtained by cooperating cam surfaces. Hereto, the first housing structure 3 has a first cam surface 3a and the pump sleeve 11 has a second cam surface 11a configured to cooperate with the first cam surface 3a, to translate rotational motion of the first housing structure 3 to linear motion of the pump sleeve 11.

The pump sleeve 11 is configured to be biased towards the proximal end of the aerosol dispenser 1. The pump sleeve 11 is configured to be biased such that the second cam surface 11a bears against the first cam surface 3a. The pump sleeve 11 has an elongated needle holding structure provided with a needle (shown in FIG. 7d). The needle holding structure extends axially in the proximal direction towards a spray nozzle assembly of the aerosol dispenser 1. The needle is attached to the pump sleeve 11 inside the needle holding structure and configured to extend axially in the distal direction into the cartridge. When the pump sleeve 11 is moved axially towards the distal end of the aerosol dispenser 1 due to the above-described rotating operation, the volume of a cavity between the needle holding structure and the spray nozzle assembly is increased. An under-pressure with respect to the pressure in the cartridge, which is in fluid communication with the cavity via the needle, is thereby created in the cavity. Liquid from the cartridge is therefore pumped into the cavity. The cavity is thereby filled with a dose to be dispensed. The pump sleeve 11 is maintained in this axial loaded position until the activation member 9 is actuated. The activation member 9 is configured to release the pump sleeve 11 when the activation member 9 is actuated, i.e. pushed in the triggering position. In particular, actuation of the activation member 9 releases the biased pump sleeve 11, causing the pump sleeve 11 to return to its initial or default position. The size of the liquid-filled cavity is thus reduced as the needle holding structure is moved in the proximal direction, whereby the liquid is pushed out through the spray nozzle assembly, forming an aerosol.

Figure 3:
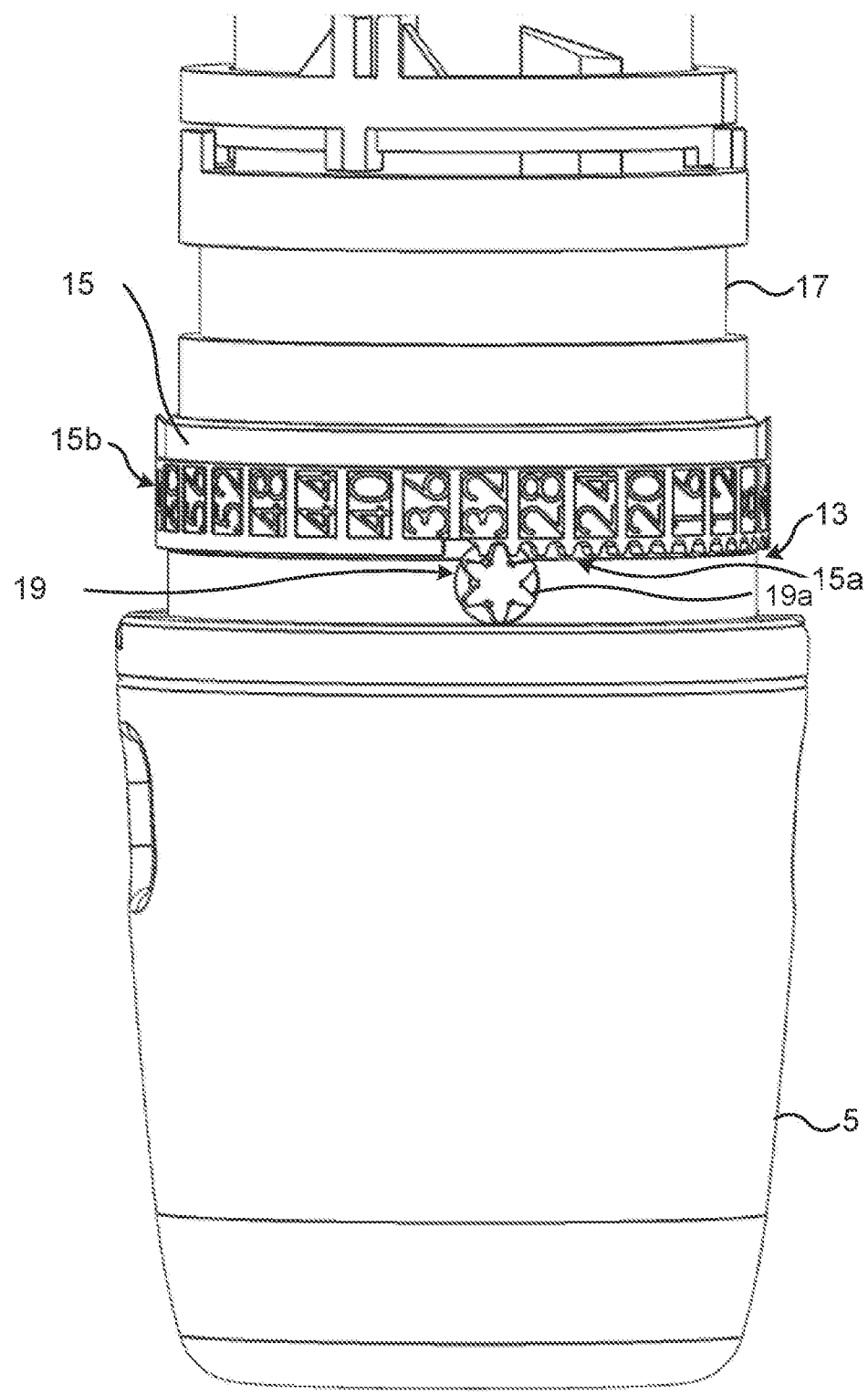
FIG. 3 shows the aerosol dispenser in FIG. 1 with a first housing structure removed to expose part of the interior of the aerosol dispenser.

Turning now to FIG. 3, the interior of the aerosol dispenser 1 is shown. The exemplified aerosol dispenser 1 comprises a dose counting mechanism 13. The dose counting mechanism 13 is configured to indicate the number of doses left in the aerosol dispenser 1. The dose counting mechanism 13 comprises an inner sleeve 17 arranged inside the second housing structure 5. The inner sleeve 17 is configured to be rotationally fixed relative to the second housing structure 5. The inner sleeve 17 is configured to engage with the second housing structure 5 to prevent relative rotation between the inner sleeve 17 and the second housing structure 5. The inner sleeve 17 extends longitudinally from the second housing structure 5 into the first housing structure 3. The inner sleeve 17 is arranged concentrically with the first housing structure 3 and with the second housing structure 5. The inner sleeve 17 is hence arranged in the second housing structure 5 and in the first housing structure 3.

The dose counting mechanism 13 comprises an annular dose counter 15. The dose counter 15 is arranged around the inner sleeve 17. In the present example, the dose counter 15 is arranged around the inner sleeve 17 in a region which extends into the first housing structure 3. The dose counter 15 is arranged concentrically with the inner sleeve 17. Alternatively, the dose counter could be arranged around the inner sleeve in a region which is within the second housing structure.

The dose counter 15 is configured to be rotatably arranged relative to the inner sleeve 17. The dose counter 15 is hence able to rotate relative to the inner sleeve 17. The dose counter 15 is configured to be rotatably arranged relative to the first housing structure 3. The dose counter 15 is hence able to rotate relative to the first housing structure 3. The dose counter 15 is provided with a plurality of teeth 15a arranged one after the other in the circumferential direction along the perimeter of the dose counter 15. In the example shown in FIG. 3, the teeth 15a are pointing axially towards the distal end of the aerosol dispenser 1. The teeth 15a are hence pointing in the distal direction.

The dose counter 15 is provided with a remaining dose scale 15b along its external perimeter. The remaining dose scale 15b provides an indication of the remaining number of doses left in the aerosol dispenser 1. The remaining dose scale 15b may for example comprise printing or etching of the number of doses left, as shown in FIG. 3. The activation member 9 is configured to display the remaining dose scale 15b through the dose display 9a, which in the present example is a dose window. The activation member 9 may in particular be configured to display the currently remaining number of doses through the dose display 9a, as for example can be seen in FIG. 1 where the letter "P" is shown through the dose display 9a. "P" stands for "primer" which is a primer dose that may be dispensed before the first dose used by the user is dispensed.

The dose counting mechanism 13 furthermore comprises an actuator 19. The actuator 19 is rotatable. The actuator 19 is configured to be rotatably attached to the inner sleeve 17. The actuator 19 may be configured to freely rotate relative to the inner sleeve 17 about an axis which is perpendicular to the central axis D. The exemplified actuator 19 extends radially outwards from the inner sleeve 17. The actuator 19 may have a radially extending axle and the actuator 19 may be attached to the inner sleeve 17 by means of the axle, which may extend into or through the wall of the inner sleeve 17. The actuator 19 is configured to at least partly radially align with the dose counter 15. In particular, the actuator 19 is configured to engage with the teeth 15a of the dose counter 15. The actuator 19 may for example be a cogwheel. The actuator 19 in the form of a cogwheel may be provided with cogs configured to mesh with the teeth 15a of the dose counter 15. Rotation of the dose counter 15 hence causes rotation of the actuator 19. Rotation of the actuator 19 may also cause rotation of the dose counter 15, as will be explained in more detail in the following.

Figure 4:
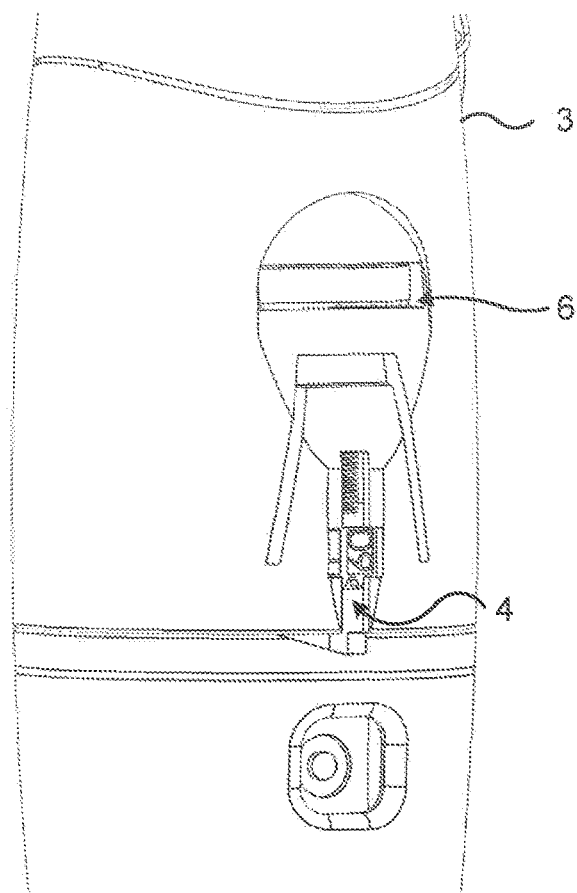
FIG. 4 shows a perspective view of a portion of the aerosol dispenser in FIG. 1 with an activation member removed.

FIG. 4 shows the first housing structure 3 without the activation member 9. The first housing structure 3 has an axial track or groove 4. The track 4 is configured to engage with the activation member 9, enabling the activation member 9 to run axially in the track 4 between the non-triggering position and the triggering position. The first housing structure 3 furthermore has an actuation member opening 6, which is a through-opening extending radially through the wall of the first housing structure 3. The actuation member opening 6 is in the present example a circumferentially extending slit.

Figure 5A:
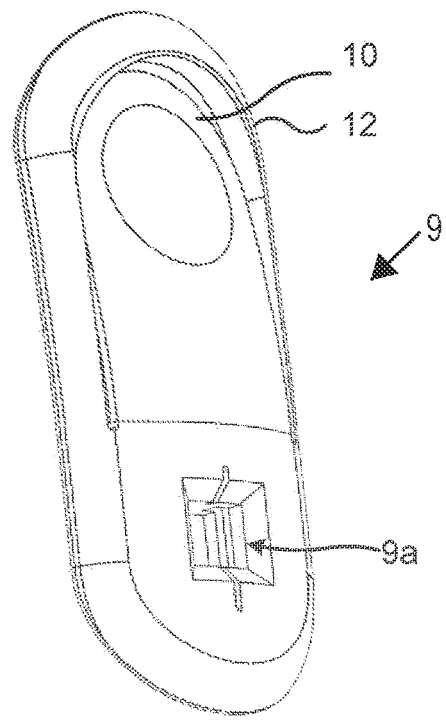
FIG. 5a is a perspective view of the activation member.

FIG. 5a shows a perspective view of the activation member 9. The activation member 9 has a tab portion 10. The tab portion 10 is radially flexible. According to the present example, the activation member 9 has an outer frame 12, which surrounds the tab portion 10. The tab portion 10 is configured to flex radially relative to the outer frame 12.

Figure 5B:
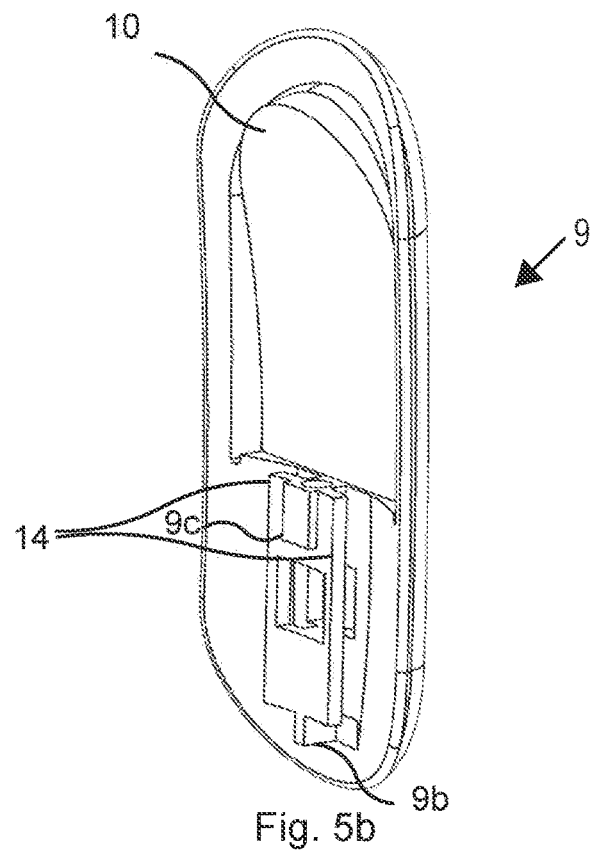
FIG. 5b is a perspective view of the activation member.

FIG. 5b shows a radially inner side of the activation member 9. The activation member 9 has wings 14 configured to engage with the track 4 of the first housing structure 3. The wings 14 enable the activation member 9 to run in the track 4. The activation member 9 furthermore has a guide heel 9b which sets the axial position of the activation member 9 relative to the first housing member 3 when the second housing structure 5 is being rotated relative to the first housing structure 3. The guide heel 9b extends distally from the wings 14. The activation member 9 also has a blocking heel 9c configured to cooperate with the dose counter 15. The blocking heel 9c protrudes radially inwards from the wings 14.

Figure 6:
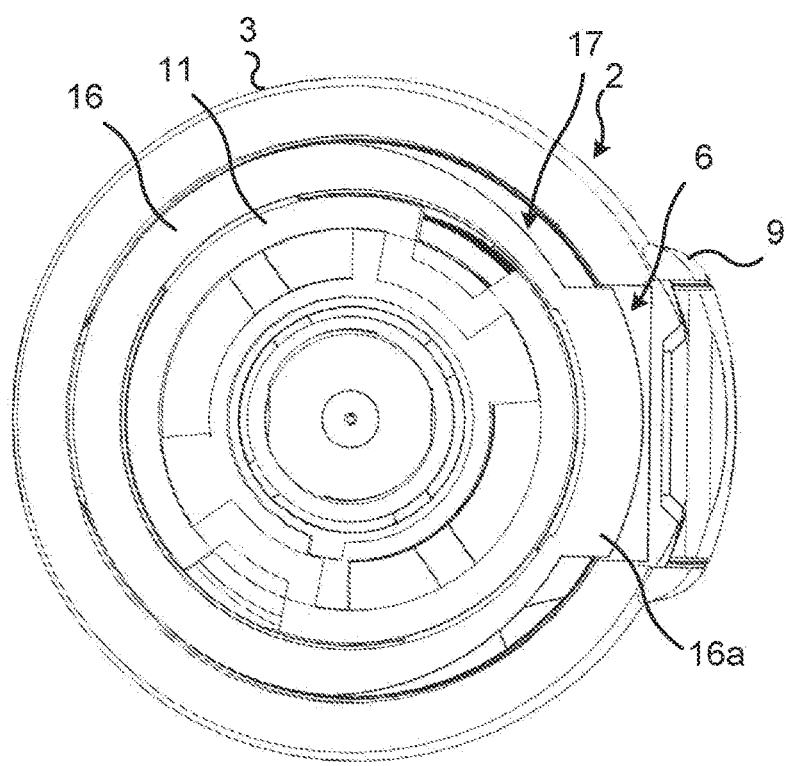
FIG. 6 is a cross-section along lines B-B in FIG. 1.

FIG. 6 shows a cross-section of the aerosol dispenser 1 along lines B-B in FIG. 1. As shown in FIG. 6, the aerosol dispenser 1 comprises an actuation member 16. The first housing structure 3, the activation member 9 and the actuation member 16 form part of an activation mechanism 2.

The actuation member 16 may be generally annular and is in FIG. 6 exemplified by an actuation ring. The first housing structure 3 is configured to receive the actuation member 16. The actuation member 16 is configured to be movable inside the first housing structure 3. Preferably, the actuation member 16 is movable in a transverse plane to the central axis D. The actuation member 16 may be rotationally locked relative to the first housing member 3. The inner surface of the first housing structure 3 may for example be provided with one or more radially inwards extending ribs and the actuation member 16 may have one or more recesses configured to engage with a respective rib.

The actuation member 16 is configured to receive a portion of the pump sleeve 11. The actuation member 16 is configured to be arranged on a radial surface 26 of the inner sleeve 17. The inner sleeve 17 is hence configured to support the actuation member 16. The actuation member opening 6 is configured to receive a portion of the actuation member 16. The actuation member 16 has a radially outwards extending protrusion 16a configured to be received by the actuation member opening 6. The actuation member 16 may narrow radially on both peripheral sides of the protrusion 16a. Hereto, the actuation member 16 may have a different radial width in the peripheral direction to enable movement of the actuation member 16 relative to the first housing structure 3 in the transverse plane. The actuation member 16 is configured to be essentially centred on the central axis of the first housing structure 3 when the pump sleeve 11 is moved distally through the actuation member 16 towards the loaded position, as shown in FIG. 6. When the pump sleeve 11 has reached its loaded position, the inner sleeve 17 is configured to push the actuation member 16 to an offset position relative to the central axis D. As a result, the protrusion 16a is further received by the actuation member opening 6. In this position of the pump sleeve 11, a radial surface of the pump sleeve 11 has moved distally past a distal end radial surface of the actuation member 16. The actuation member 16 is hence set in a position in which a radial surface of the pump sleeve 11 bears against a corresponding facing radial surface of the actuation member 16. The actuation member 16 hence prevents the biased pump sleeve 11 from moving proximally towards its default position. The pump sleeve 11 is hence maintained in the loaded position.

Figure 7A:
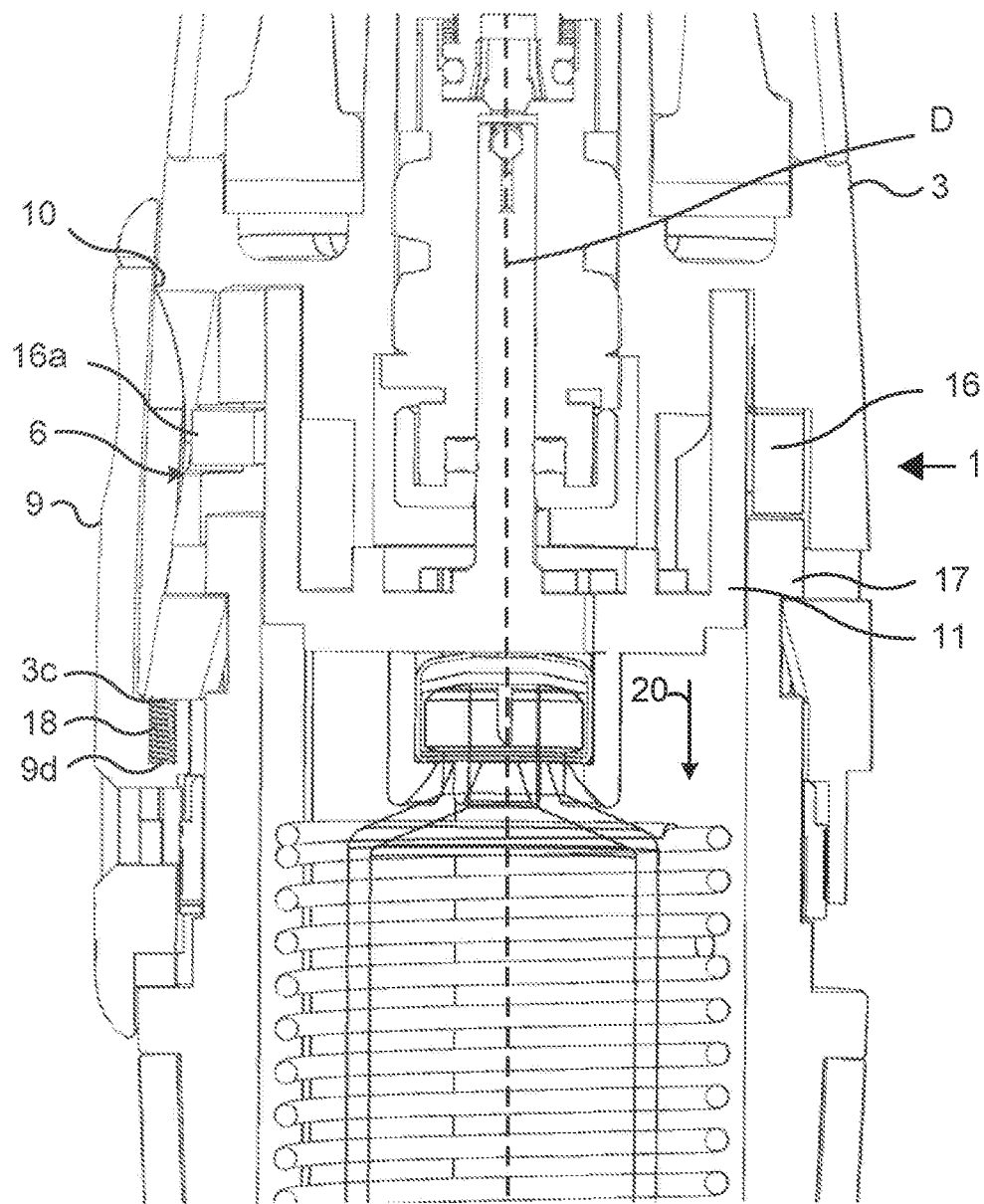
FIG. 7a shows a state of an activation mechanism when the aerosol dispenser in FIG. 1 is being operated.

FIG. 7a shows a longitudinal section of a portion of the aerosol dispenser 1. The exemplified aerosol dispenser 1 comprises a resilient member 18 configured to bias the activation member 9 towards the triggering position. The activation member 9 may for example have an axial channel 9d configured to receive the resilient member 18 and the first housing structure 3 may have a radial surface 3c aligned with and facing the opening of the channel 9d such that the resilient member 18 accumulates more energy when the activation member 9 is moved towards the non-triggering position.

In FIG. 7a, the activation member 9 is in the non-triggering position. The actuation member 16 is centred or essentially centred on the central axis D of the aerosol dispenser 1, allowing the pump sleeve 11 to move in the distal direction through the central opening of the actuation member 16 as shown by arrow 20 towards the loaded position. The tab portion 10 of the activation member 9 bears against the outer surface of the first housing structure 3. The tab portion 10 is thus prevented by the first housing structure 3 from being flexed radially inwards.

Figure 7B:
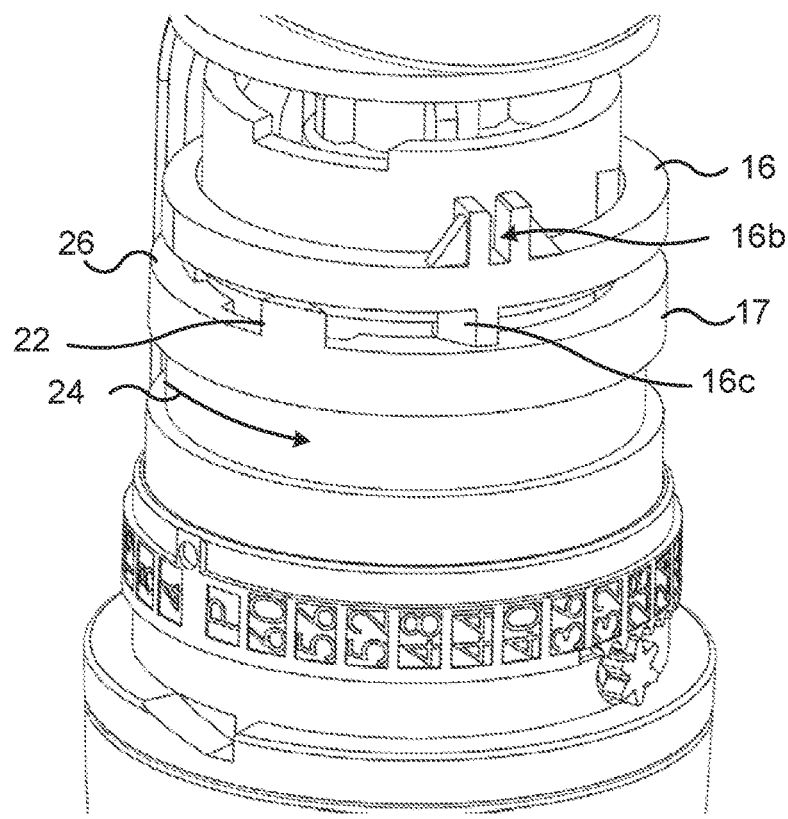
FIG. 7b shows a state of an activation mechanism when the aerosol dispenser in FIG. 1 is being operated.

FIG. 7b shows the state in FIG. 7a from a different view, with the first housing structure 3 removed. The actuation member 16 rests on a radial surface 26 of the inner sleeve 17. The depicted actuation member 16 is provided with a radial recess 16b configured to engage with a corresponding radially inwards extending rib on the inner surface of the first housing structure 3 to prevent relative rotation between the actuation member 16 and the first housing structure 3.

The actuation member 16 has a cam structure 16c protruding in the distal direction from the main body of the actuation member 16. The inner sleeve 17 has a second cam structure 22 configured to cooperate with the first cam structure 16c. In particular, when the inner sleeve 17 is rotated in the direction 24 the first cam structure 16c and the second cam structure 22 will eventually abut/cooperate, causing the actuation member 16 to move essentially linearly in the transverse plane from the inner surface of the first housing structure 3 in the region of the first cam structure 16c towards the opposite inner wall and further into the actuation member opening 6 of the first housing structure 3. The first cam structure 16c may for example be a distally extending protrusion which is chamfered in a cross-section of the aerosol dispenser 1 and the second cam structure 22 may be a proximally extending protrusion which is chamfered in a cross-section of the aerosol dispenser 1. The actuation member 16 may be provided with several such protrusions, which may function as support elements or distancing elements which support the actuation member 16 on the radial surface 26 of the inner sleeve 17.

Figure 7C:
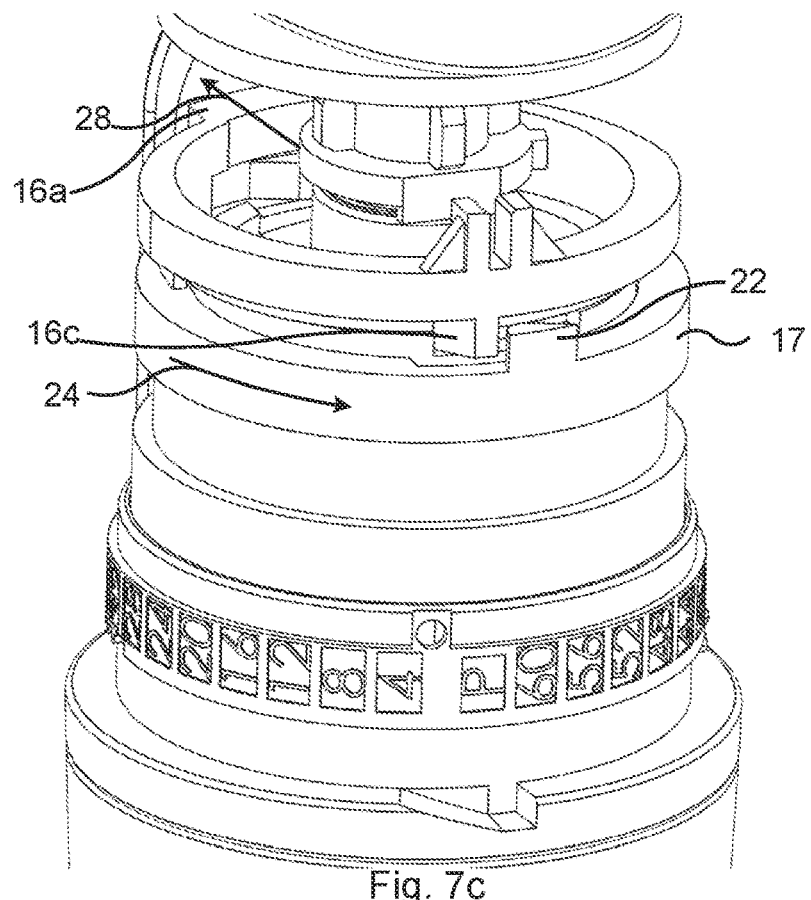
FIG. 7c shows a state of an activation mechanism when the aerosol dispenser in FIG. 1 is being operated.

In FIG. 7c, the inner sleeve 17 has been further rotated relative to the first housing structure 3, in the direction shown by arrow 24. The pump sleeve 11 has obtained the loaded position. The second cam structure 22 and the first cam structure 16c have met and this cooperation has caused a displacement of the actuation member 16 in the transverse plane of the aerosol dispenser 1. The actuation member 16 has been further received in the actuation member opening 6. In particular, the protrusion 16a of the actuation member 16 has been further pushed into the actuation member opening 6.

Figure 7D:
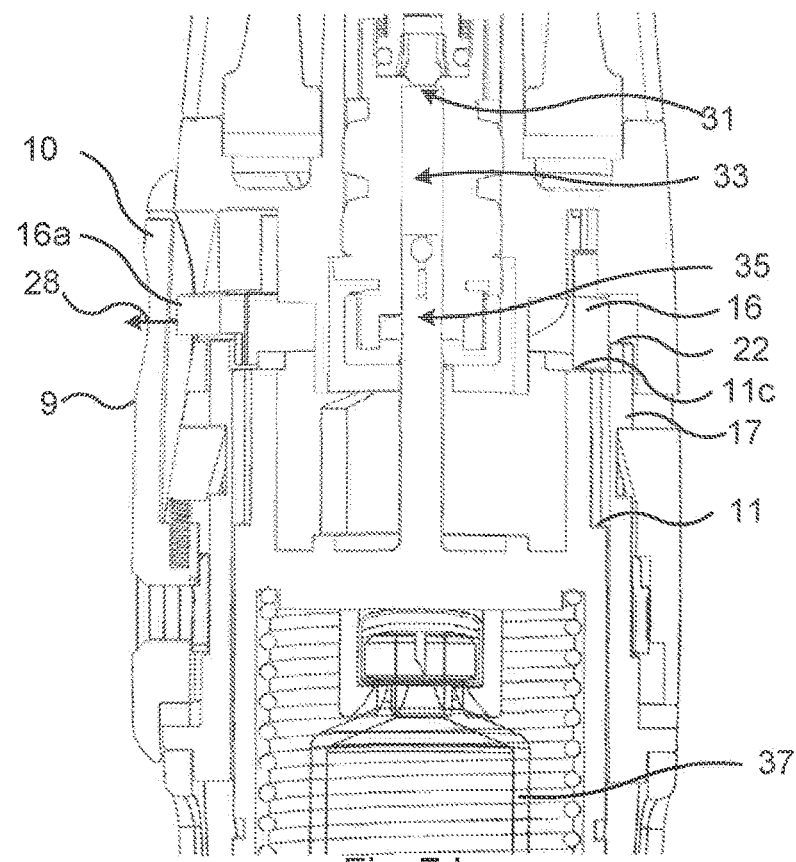
FIG. 7d shows a state of an activation mechanism when the aerosol dispenser in FIG. 1 is being operated.

FIG. 7d shows this state of the aerosol dispenser 1 in a longitudinal section. In addition to the above, the activation member 9 has been slid to the triggering position. The activation member 9 has hence been moved in the distal direction. The tab portion 10 has therefore also been moved in the distal direction such that radial inwards flexing is now enabled. A user is hence able to push the tab portion 10 radially inwards. The pump sleeve 11 has a radial surface 11c which has moved past the actuation member 16 in the proximal direction and which bears against the actuation member 16, due to the movement of the actuation member 16 caused by the cooperating first and second cam structures 16c and 22.

In FIG. 7d, the cavity 33 between the spray nozzle assembly 31 and the needle holding structure 35 is shown. The cavity 33 is filled with liquid pumped from a cartridge 37 attached to the pump sleeve 11.

Figure 7E:
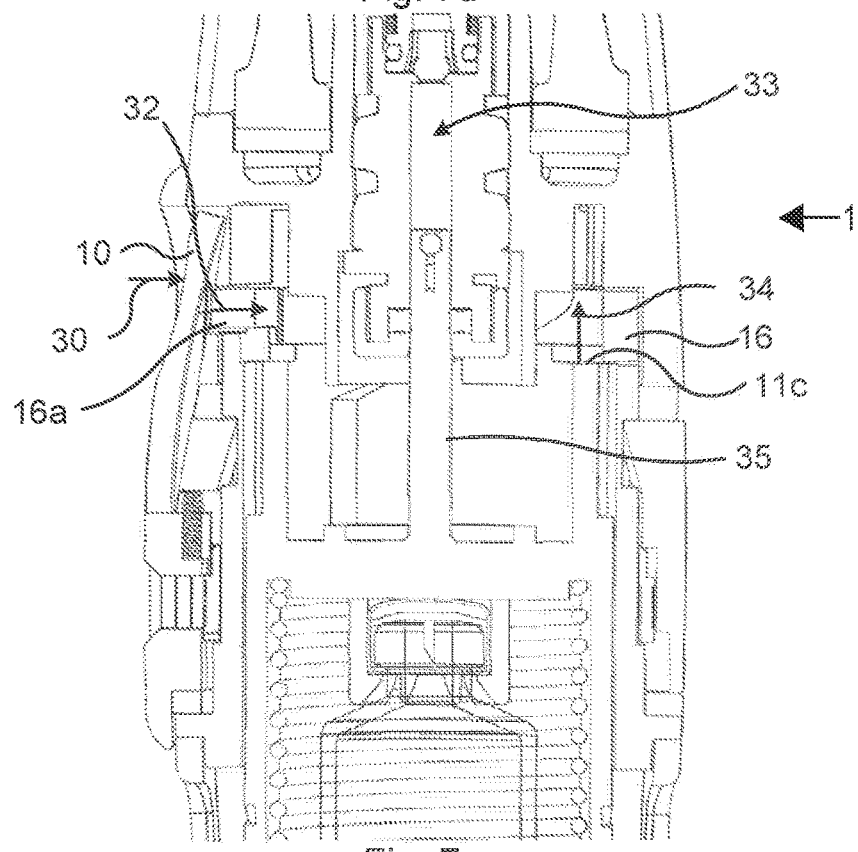
FIG. 7e shows a state of an activation mechanism when the aerosol dispenser in FIG. 1 is being operated.

FIG. 7e depicts a state of the aerosol dispenser 1 in which the tab portion 10 has been pushed radially inwards, as shown by arrow 30. The tab portion 10 thereby contacts and acts on the actuation member 16, and in particular the protrusion 16a, causing displacement of the actuation member 16 in the transverse plane as shown by arrow 32 towards the opposite inner wall of the first housing structure 3. The actuation member 16 is hence pushed back towards its initial position, whereby the actuation member 16 is moved from the position in which it blocks the biased pump sleeve 11 from proximal movement. The pump sleeve 11 will hence return to its default position as indicated by arrow 34. The needle holding structure 35 will thus move in the proximal direction and reduce the volume of the cavity 33, causing the aerosol dispenser 1 to dispense the liquid contained in the cavity 33.

Figure 8:
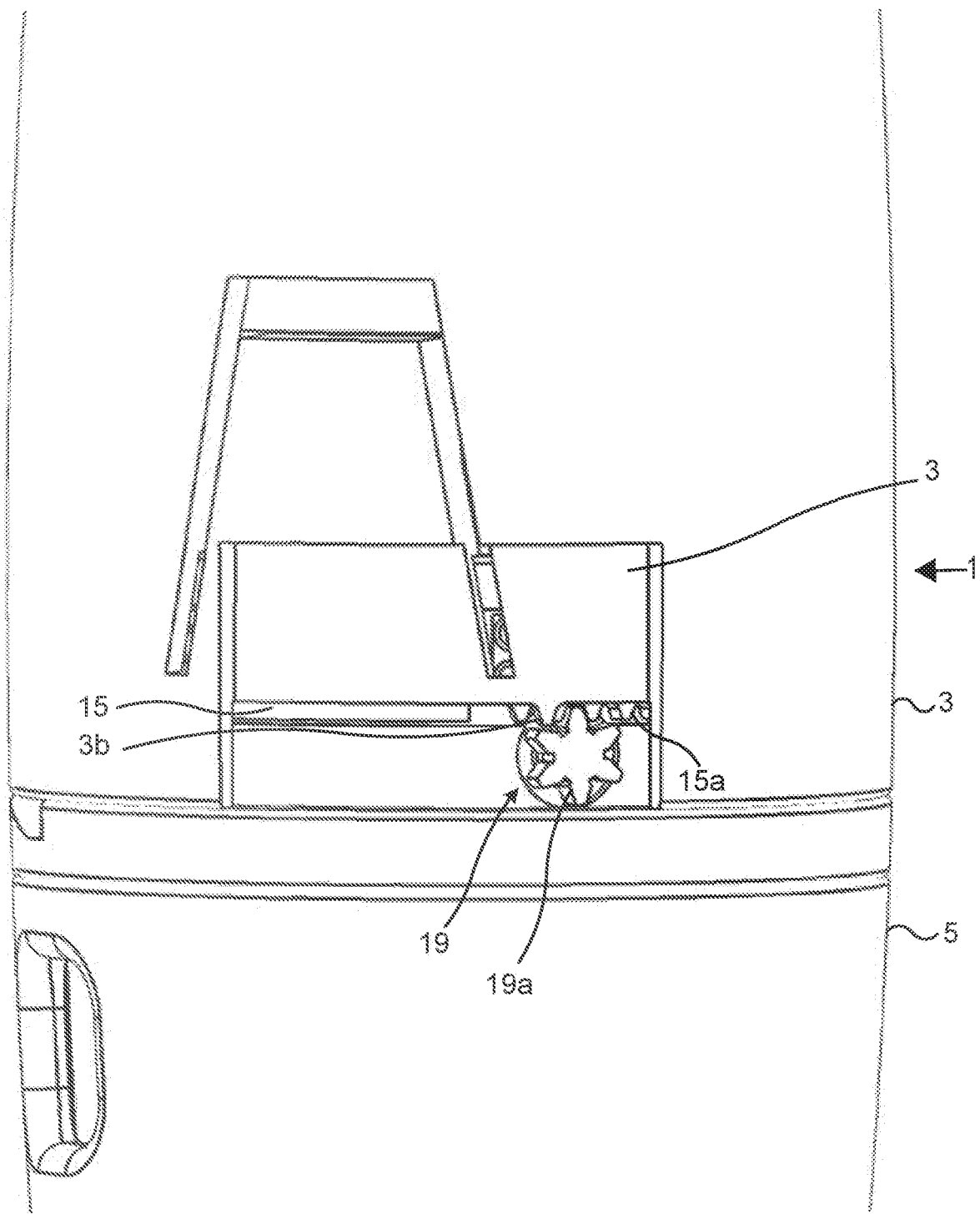
FIG. 8 shows a close-up view of the aerosol dispenser in FIG. 1 having been rotated about it central axis and with a cut-out portion to expose internal components.

FIG. 8 shows the aerosol dispenser 1 with a portion of the first housing structure 3 removed to expose further components of the dose counting mechanism 13. The dose counting mechanism 13 furthermore comprises a rotator 3b. The rotator 3b is configured to cause movement of the actuator 19. The rotator 3b is configured to rotate the actuator 19.

The exemplified rotator 3b is fixed relative to the first housing structure 3. The rotator 3b may form part of the first housing structure 3. For example the first housing structure 3 may have an inner surface flange or cut-out and the rotator 3b may extend from the flange or radial surface of the cut-out towards the actuator 19. The rotator 3b may be a protrusion or tooth which points axially towards the distal end of the aerosol dispenser 1. The rotator 3b may for example comprise a single protrusion or tooth or more than one protrusion or tooth.

The rotator 3b is configured to engage with the actuator 19. The rotator 3b is configured to be arranged radially adjacent to the dose counter 15. The rotator 3b may be arranged radially outside of the dose counter 15. The actuator 19 may have a thickness or extension in the radial direction such that it is able to engage with the rotator 3b and with the teeth 15a of the dose counter 15 simultaneously.

Thus, when the second housing structure 5 is being rotated relative to the first housing structure 3, the rotator 3b engages with the actuator 19, causing the actuator 19 to rotate an amount corresponding to movement of one tooth 19a of the actuator 19 from one side of the rotator 3b to the other side thereof, i.e. from one flank to the other flank of the rotator 3b. The rotator 3b is hence configured to drive the actuator 19. Since the actuator 19 simultaneously engages with the teeth 15a of the dose counter 15, the dose counter 15 is rotated about the central axis of the aerosol dispenser 1. This rotation may correspond to the pitch of the teeth 15a, i.e. the tooth to tooth or flank to flank distance. Since the dose counter 15 is provided with the remaining dose scale, the remaining number of doses as shown in the dose display 9a of the activation member 9 will be updated, in particular counted down. In case not all of the doses are displayed on the remaining dose scale 15b, but only for example every $N^{th}$ dose, then the number of teeth 15a between two visual indications on the remaining dose scale 15b may for example be N and so the dose counter 15 will be rotated such that the activation member 9 displays dose n+N instead of dose n when the aerosol dispenser 1 has been activated and triggered N times.

Once the actuator 19 has meshed with and passed the rotator 3b the actuator 19 is rotated freely by it meshing with the teeth 15a of the dose counter 15, as the inner sleeve 17 is being further rotated relative to the first body member 3. No additional rotation of the dose counter 15 is hence provided, since in this case the dose counter 15 drives the actuator 19.

Figure 9:
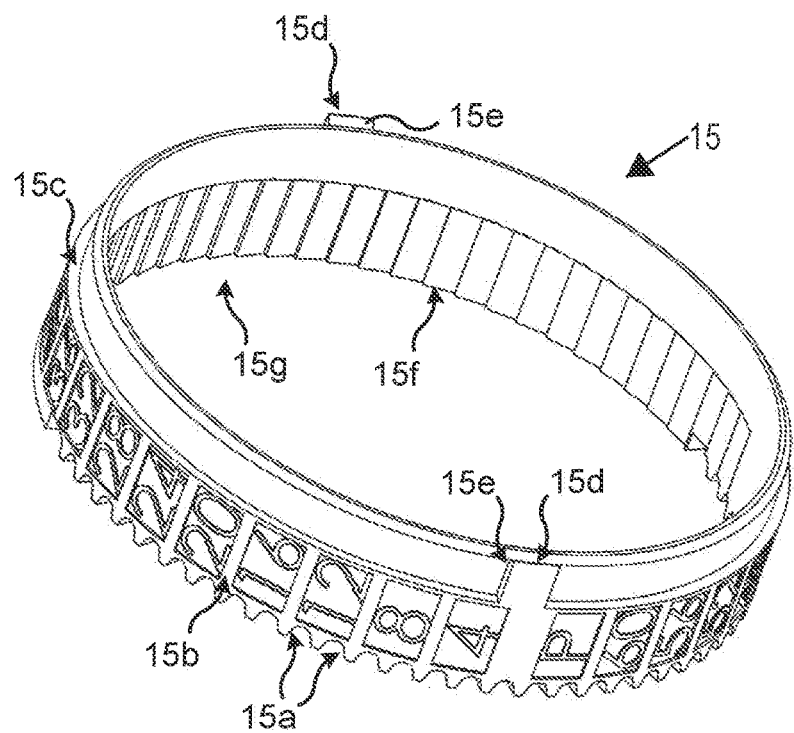
FIG. 9 is a perspective view of an example of a dose counter.

FIG. 9 shows a perspective view of the dose counter 15. The exemplified dose counter 15 comprises a flange surface 15c. The dose counter 15 comprises one or more an axial tab(s) 15d extending axially from the flange surface 15c. In the present example, the axial tab 15d extends axially from the flange surface 15c in the proximal direction. The axial tab 15d may have a chamfered end face 15e in a longitudinal section of the aerosol dispenser 1. The tab 15d is preferably arranged axially aligned with the empty dose indication of the remaining dose scale 15b.

According to the present example, the teeth 15a are provided only along about 180 degrees of the perimeter of the dose counter 15. Alternatively, the teeth could extend for example along the entire perimeter.

The dose counter 15 may be provided with a plurality of ratchet teeth 15f. The dose counter 15 has an inner perimeter surface 15g and the inner perimeter surface 15g may be provided with the ratchet teeth 15f. The ratchet teeth 15f are configured to enable rotation of the dose counter 15 in a first direction which is the dose countdown direction. The ratchet teeth 15f are configured to prevent rotation of the dose counter 15 in a second direction opposite to the first direction. It can thereby be ensured that the doses indicated by the dose display 9a are the actual number of doses remaining in the aerosol dispenser 1.

Figure 10:
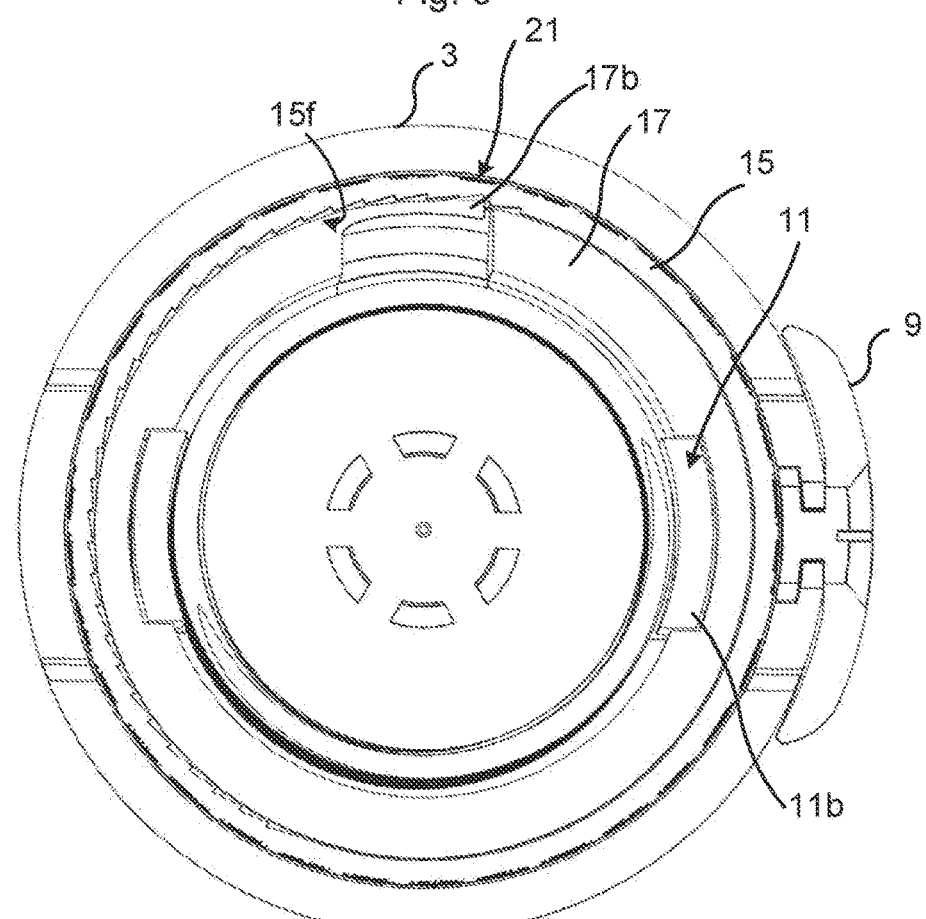
FIG. 10 is a cross-section of the aerosol dispenser along lines A-A.

FIG. 10 is a cross-section along lines A-A in FIG. 1. The rotational locking between the inner sleeve 17 and the pump sleeve 11 can be seen. In this example, the pump sleeve 11 has axial ribs 11b extending radially outwards and the inner sleeve 17 has corresponding recesses configured to receive a respective one of the axial ribs 11b. This configuration allows relative axial displacement between the pump sleeve 11 and the inner sleeve 17.

The inner sleeve 17 comprises a ratchet arm 17b configured to cooperate with the ratchet teeth 15f of the dose counter 15. The ratchet arm 17b is radially flexible and extends radially outwards and is configured to engage with the ratchet teeth 15f. The ratchet teeth 15f and the ratchet arm 17b form a ratchet mechanism 21.

Figure 11:
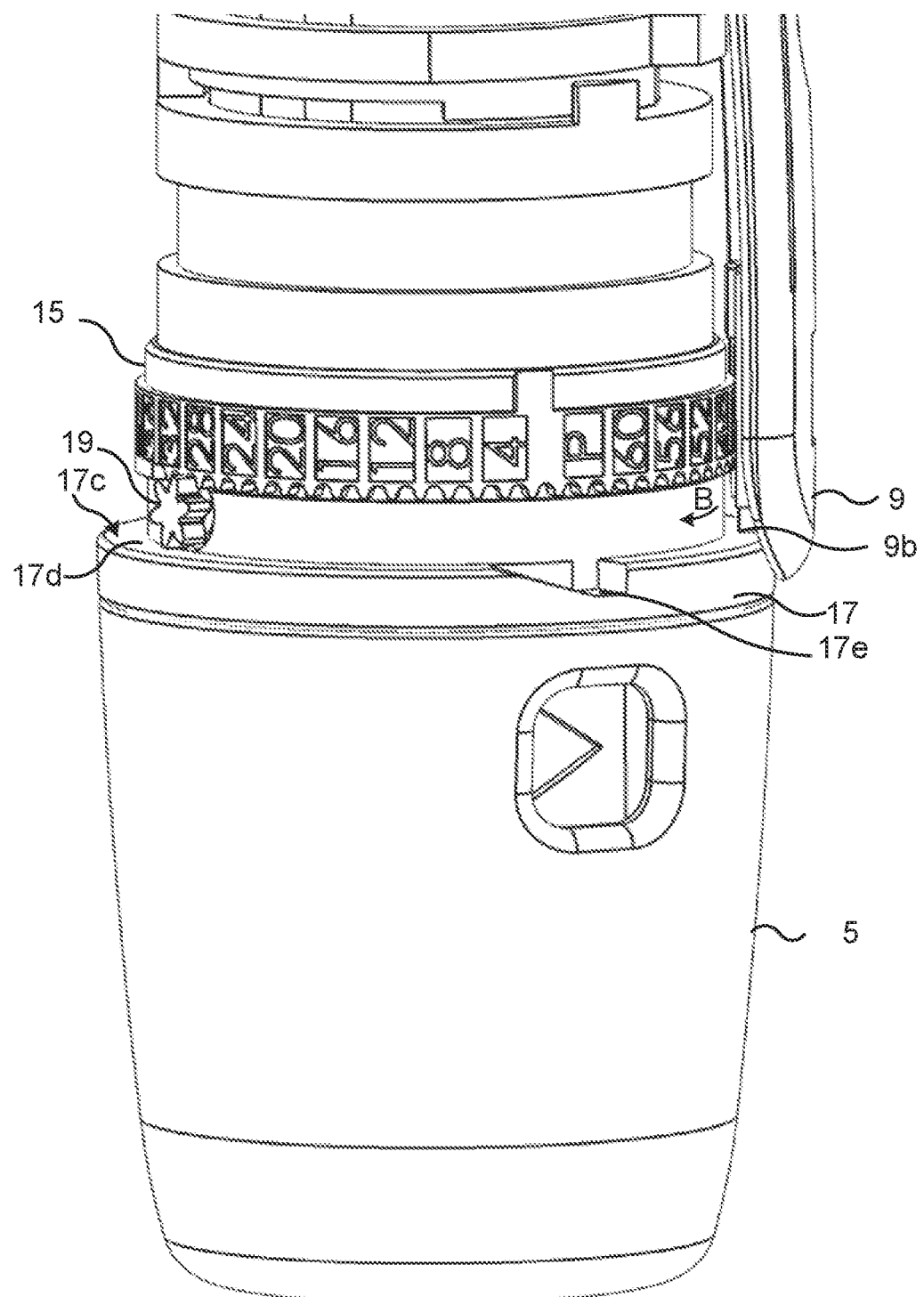
FIG. 11 is a perspective view of the aerosol dispenser in FIG. 1 with the first housing structure removed.

FIG. 11 further depicts the operation of the activation member 9. The inner sleeve 17 comprises a flange structure 17c which defines a radial flange surface 17d facing the proximal end of the aerosol dispenser 1. The radius of the inner sleeve 17 hence becomes smaller adjacent to the radial surface, in the proximal direction of the aerosol dispenser 1. The actuator 19 is mounted to the inner sleeve 17 in this region with a smaller radius. The dose counter is mounted around this region of the inner sleeve 17, proximally from the actuator 19. The flange structure 17c is provided with an axial recess 17e. Hereto, the radial flange surface 17d is provided with the axial recess 17e. The axial recess 17e has a stepped axial depth configuration at one end thereof in the peripheral direction and a gradually smoothly increasing axial depth at the opposite end. The activation member 9 has a guide heel 9b. The activation member 9 is configured to bear against the radial flange surface 17d by means of the guide heel 9b. Thus, as the second housing structure 5 and thus the inner sleeve 17 is being rotated relative to the first housing structure 3, the activation member 9 will slide along the radial flange surface 17d. When the guide heal 9b rests against the radial flange surface 17d outside of the axial recess 17e, the activation member 9 is in the non-triggering position. The activation member 9 may be biased towards the triggering position. However, when the activation member 9 moves in the direction B and the guide heel 9b eventually aligns with the axial recess 17e, the activation member 9 will be able to be moved in the distal direction from the non-triggering position to the triggering position in which the guide heel 9b rests in the axial recess 17e. Triggering of the aerosol dispenser 1 is thereby enabled. In a subsequent activation or loading operation, the activation member 9 is able to move out from the axial recess 17e into the non-triggering position until the first housing structure 3 has been rotated for example about 180 degrees, where an additional axial recess of the same type as axial recess 17e may be provided, allowing the activation member 9 to move to the triggering position.

Figure 12A:
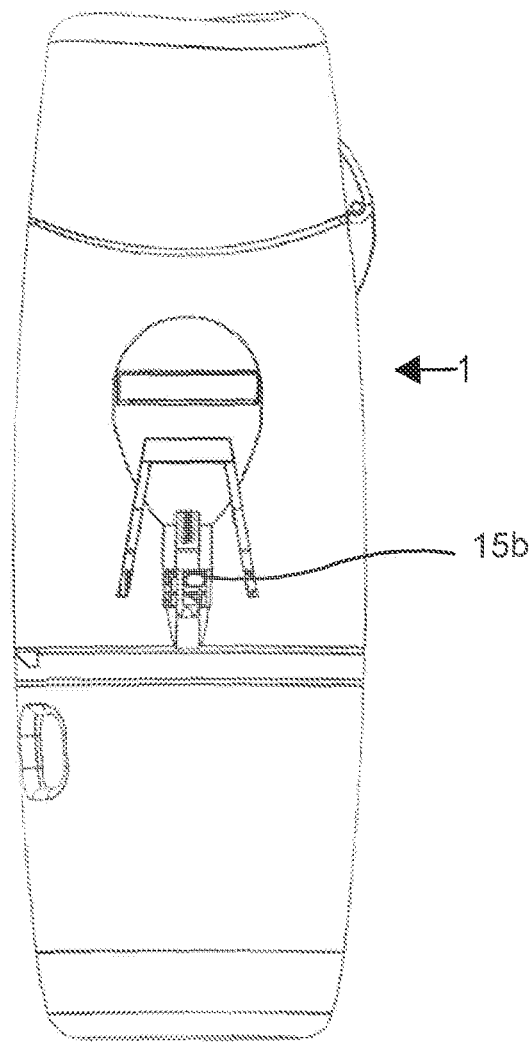
FIG. 12a depicts the aerosol dispenser in a state of operation.
Figure 12B:
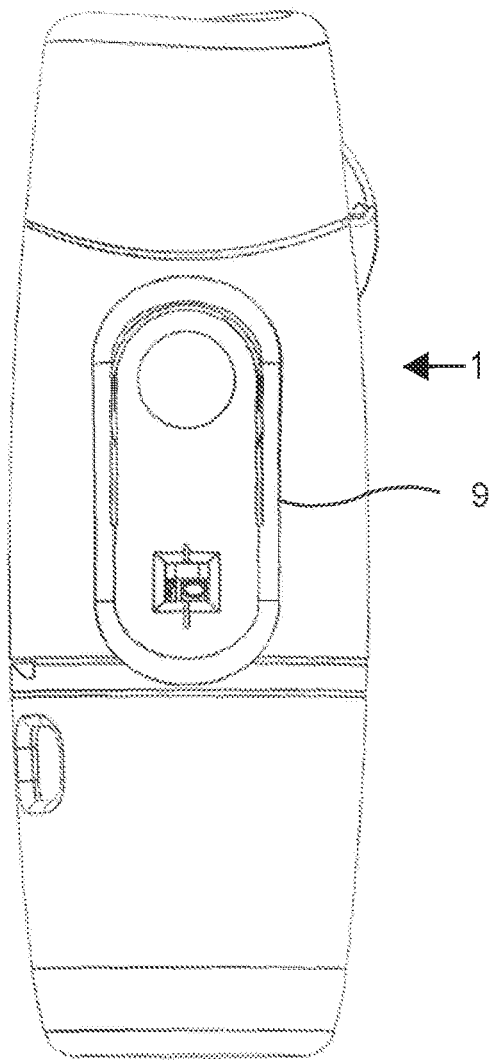
FIG. 12b depicts the aerosol dispenser in a state of operation.
Figure 12C:
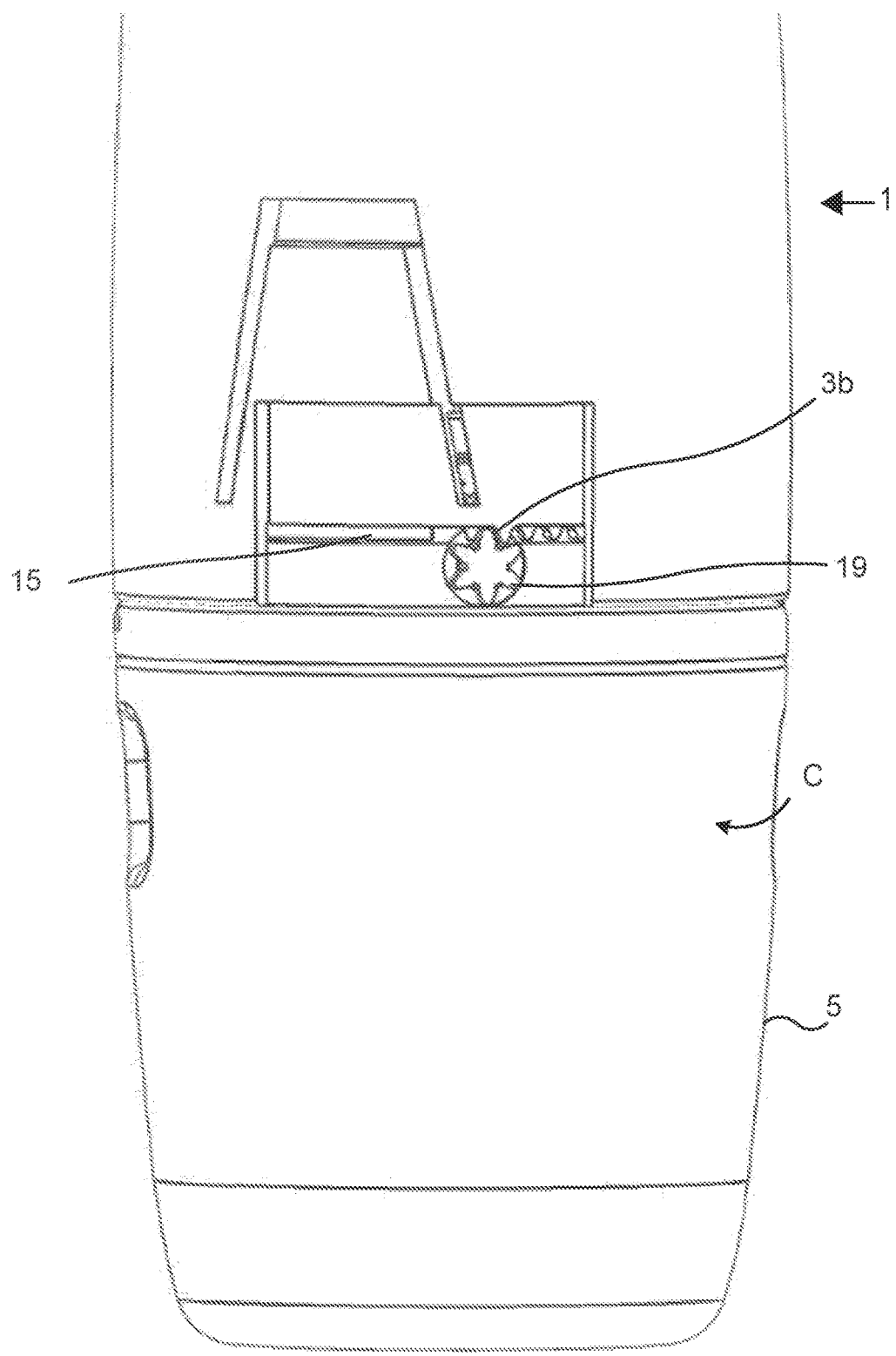
FIG. 12c depicts the aerosol dispenser in a state of operation.

The operation of the aerosol dispenser 1 and in particular of the locking mechanism will now be described in more detail with reference to FIGS. 12a-14. FIG. 12a shows the aerosol dispenser 1 without the activation member 9, which in this case would be in the non-triggering position. The remaining dose scale 15b shows that about 40 doses are still available. In FIG. 12b the activation member 9 is also shown. In the non-triggering position, the remaining dose scale 15b is not fully visible in the dose display 9a. FIG. 12c shows the actuator 19 prior to meshing with the rotator 3b. The second housing structure 5 is rotated in direction C which causes cooperation between the tooth 19a of the actuator 19 and the rotator 3b. The rotator 3b drives the actuator 19 which in turn drives the dose counter 15.

Figure 13A:
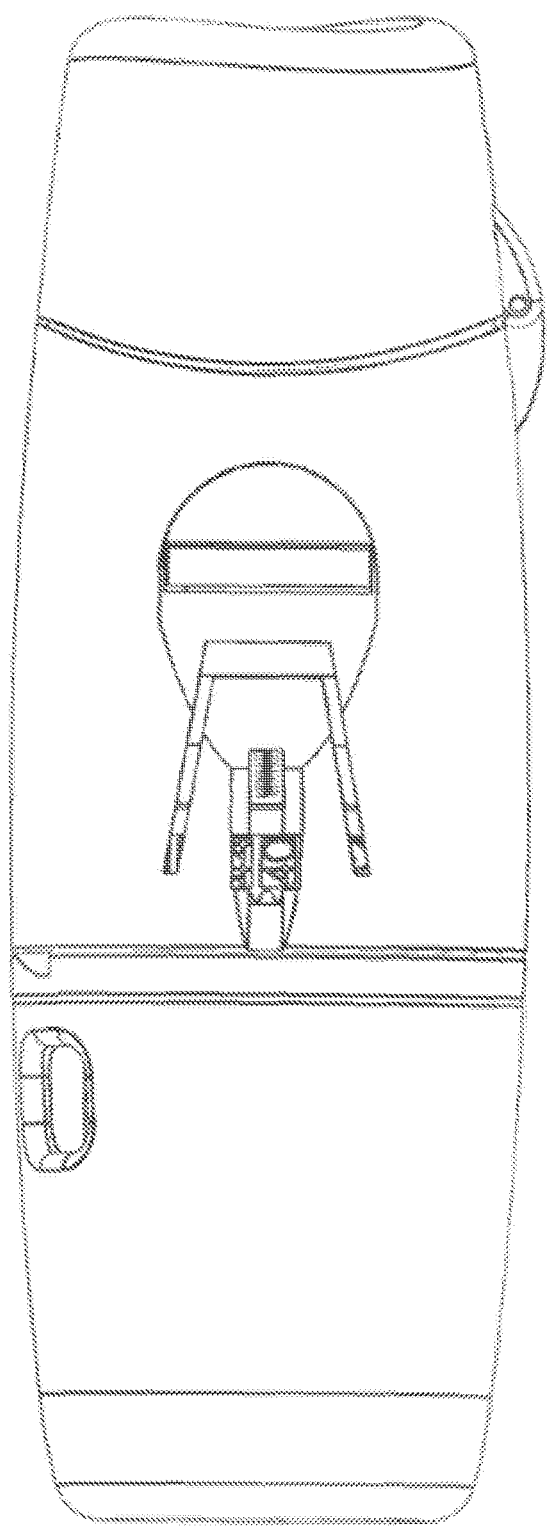
FIG. 13a depicts the aerosol dispenser in a state of operation.
Figure 13B:
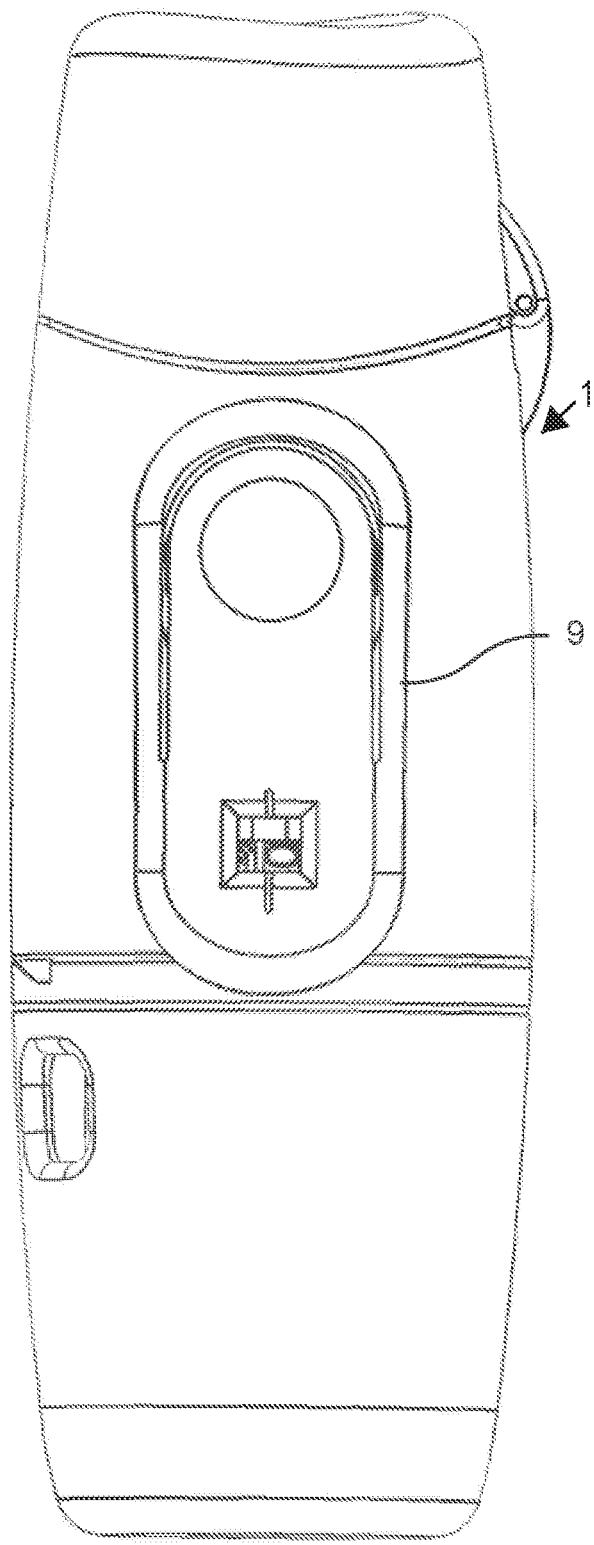
FIG. 13b depicts the aerosol dispenser in a state of operation.
Figure 13C:
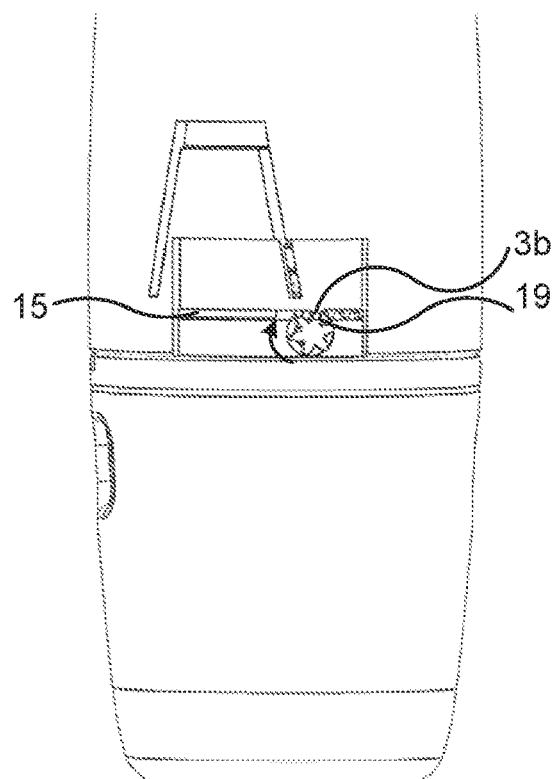
FIG. 13c depicts the aerosol dispenser in a state of operation.

In FIG. 13a the activation member 9 is removed. The remaining dose scale 15b has been rotated one increment by cooperation between the actuator 19 and the teeth 15a of the dose counter 15 and one dose has thus been dispensed. FIG. 13b shows this situation with the activation member 9 visible. In FIG. 13c it can be seen that the actuator 19 has been rotated with respect to its position in FIG. 12c such that the tooth 19b has passed the rotator 3b, i.e. the tooth 19b which in FIG. 12c bore against the left flank of the rotator 3b in the figure now bears against the right flank of the rotator 3b. The dose counter 15 has thereby rotated one increment.

Figure 14:
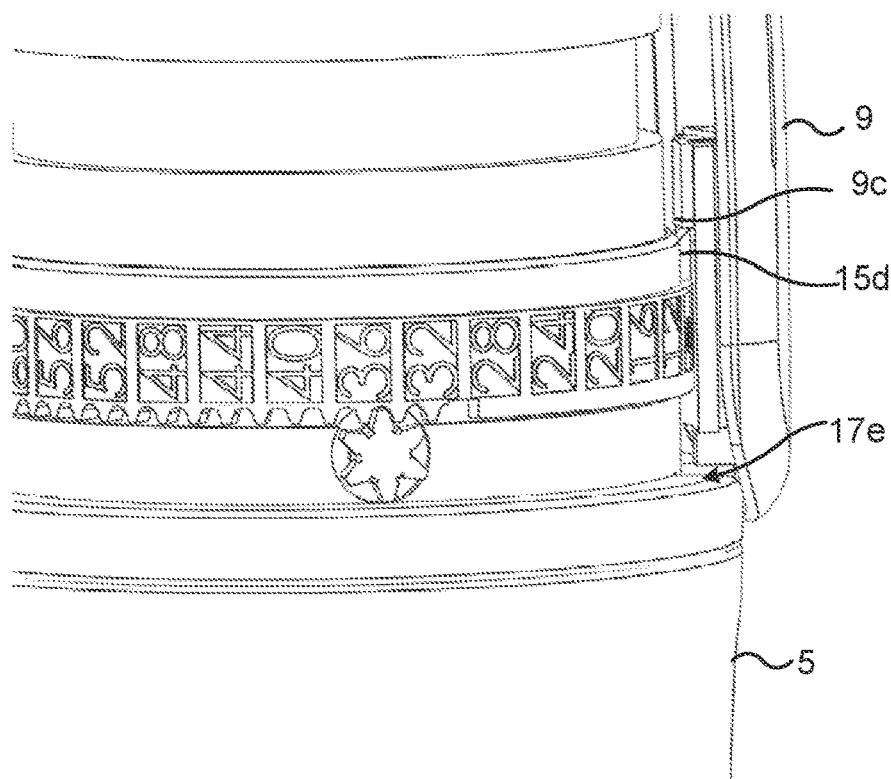
FIG. 14 depicts the aerosol dispenser in a state of operation.

FIG. 14 shows a situation in which the final dose has been dispensed from the aerosol dispenser 1. The aerosol dispenser 1 has been loaded by rotation of the second housing structure 5 relative to the first housing structure 3. The activation member 9 has thus been aligned with the axial recess 17e. The activation member 9 has a blocking heel 9c extending radially inwards and configured to align and bear against the tab 15d of the dose counter 15 when the dose counter 15 has been rotated to display that that there are no more doses available, i.e. when remaining dose is the empty dose indication. The blocking heel 9c is in this case arranged proximally relative to the tab 15d. The activation member 9 is thereby prevented from moving from the non-triggering position to the triggering position. A user will hence become aware of that the no further doses are available in the aerosol dispenser 1.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An activation mechanism for an aerosol dispenser, wherein the activation mechanism comprises:
   a first housing structure,
   an actuation member movably arranged in the first housing structure, wherein the first housing structure is provided with an actuation member opening aligned with an axial position of the actuation member,
   an inner sleeve configured to be rotatably attached to the first housing structure, and
   an activation member configured to be slidably attached to the first housing structure, the activation member being configured to slide between a non-triggering position and a triggering position relative to the first housing structure,
   wherein the activation member has a radially flexible tab portion, the tab portion being arranged offset from the actuation member opening when the activation member is in the non-triggering position, restricting radial flexing of the tab portion, and wherein the tab portion is configured to align with the actuation member opening when the activation member is in the triggering position, thereby enabling the tab portion to flex radially inwards to cause movement of the actuation member.

2. The activation mechanism as claimed in claim 1, wherein the first housing structure has a central axis and the actuation member is movable in a transverse plane relative to the central axis.

3. The activation mechanism as claimed in claim 2, wherein the actuation member is generally annular and arranged offset from the central axis when the activation member is in the non-triggering position.

4. The activation mechanism as claimed in claim 1, wherein the actuation member has a radially outwards extending protrusion configured to extend into the actuation member opening and wherein the actuation member narrows radially on a first peripheral side of the protrusion and a second peripheral side of the protrusion.

5. The activation mechanism as claimed in claim 1, wherein the actuation member is configured to be rotationally locked relative to the first housing structure.

6. The activation mechanism as claimed in claim 1, comprising a pump sleeve configured to be rotationally locked relative to the inner sleeve, wherein the pump sleeve is configured to be rotatable relative to the first housing structure and configured to move axially relative to the first housing structure and the inner sleeve, wherein the pump sleeve is configured to cooperate with the first housing structure such that rotation of the first housing structure relative to the inner sleeve causes axial displacement of the pump sleeve relative to the first housing structure and relative to the inner sleeve, the pump sleeve thereby moving from a default position to a loaded position.

7. The activation mechanism as claimed in claim 6, wherein the actuation member is configured to lock the pump sleeve in the loaded position, and wherein the actuation member is configured to release the pump sleeve from the loaded position when moved by the tab portion.

8. The activation mechanism as claimed in claim 1, wherein the inner sleeve has a radial flange surface, wherein the activation member is configured to rest on the flange surface, whereby rotation of the inner sleeve relative to the first housing structure causes movement of the activation member along the flange surface.

9. The activation mechanism as claimed in claim 8, wherein the flange surface has an axial recess configured to receive a portion of the activation member when the inner sleeve is rotated relative to the first housing structure, thereby allowing movement of the activation member from the non-triggering position to the triggering position.

10. The activation mechanism as claimed in claim 9, comprising a dose counter configured to be arranged coaxially with the first housing structure and the inner sleeve, wherein the dose counter is configured to rotate relative to the first housing structure and the inner sleeve, the dose counter having a remaining dose scale and the dose counter being provided with an axial tab configured to bear against the activation member when the remaining dose scale indicates that no further doses are available, to prevent the activation member to move from the non-triggering position to the triggering position.

11. The activation mechanism as claimed in claim 10, wherein the activation member has a guide heel arranged proximally relative to the axial tab, wherein the guide heel is configured to bear against the axial tab of the dose counter when the remaining dose scale indicates that no further doses are available.

12. The activation mechanism as claimed in claim 1, wherein the activation member is configured to be biased towards the triggering position.

13. The activation mechanism as claimed in claim 1, wherein the first housing structure is provided with an axially extending track and the activation member has wings (14) configured to run in the track to guide sliding movement of the activation member.

14. An aerosol dispenser comprising an activation mechanism as claimed in claim 1.

15. An activation mechanism for an aerosol dispenser, wherein the activation mechanism comprises:
a first housing structure;
an actuation member movably arranged in the first housing structure, wherein the first housing structure is provided with an actuation member opening aligned with an axial position of the actuation member;
an activation member configured to be slidably attached to the first housing structure, where the activation member being configured to slide between a non-triggering position and a triggering position relative to the first housing structure; and
an inner sleeve rotatably attached to the first housing structure,
wherein the activation member is rotatably attached to the first housing structure and has a radially flexible tab portion, the tab portion being arranged offset from the actuation member opening when the activation member is in the non-triggering position, restricting radial flexing of the tab portion, and wherein the tab portion is configured to align with the actuation member opening when the activation member is in the triggering position, thereby enabling the tab portion to flex radially inwards to cause movement of the actuation member, and
wherein the actuation member rotationally locks relative to the first housing structure.

16. The activation mechanism of claim 15 further comprising a pump sleeve configured to be rotationally locked relative to the inner sleeve, wherein the pump sleeve rotates relative to the first housing structure and moves axially relative to both the first housing structure and the inner sleeve.

17. The activation mechanism of claim 16, wherein the pump sleeve cooperates with the first housing structure such that rotation of the first housing structure relative to the inner sleeve causes axial displacement of the pump sleeve relative to the first housing structure and relative to the inner sleeve causing the pump sleeve to move from a default position to a loaded position.

18. The activation mechanism of claim 15, wherein the inner sleeve has a radial flange surface operatively engaged with the activation member such that rotation of the inner sleeve relative to the first housing structure causes movement of the activation member along the flange surface.

19. The activation mechanism of claim 18, wherein the flange surface has an axial recess that receives a portion of the activation member when the inner sleeve is rotated relative to the first housing structure, thereby allowing movement of the activation member from the non-triggering position to the triggering position.

* * * * *